US009498241B2

(12) United States Patent
Leonhard et al.

(10) Patent No.: US 9,498,241 B2
(45) Date of Patent: Nov. 22, 2016

(54) MEDICAL INSTRUMENT WITH SHAPE ADAPTIVE GRIPPING TOOL

(75) Inventors: Martin Leonhard, Emmingen (DE); Ralf Staud, Emmingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 29 days.

(21) Appl. No.: 13/035,197

(22) Filed: Feb. 25, 2011

(65) Prior Publication Data

US 2011/0213409 A1 Sep. 1, 2011

(30) Foreign Application Priority Data

Feb. 25, 2010 (DE) .................. 10 2010 009 259

(51) Int. Cl.
*A61B 17/28* (2006.01)
*A61B 17/29* (2006.01)

(52) U.S. Cl.
CPC ........ *A61B 17/29* (2013.01); *A61B 2017/2937* (2013.01)

(58) Field of Classification Search
CPC ............... A61B 2017/2932; A61B 2017/2937
USPC .................................. 606/205–209
See application file for complete search history.

(56) References Cited

U.S. PATENT DOCUMENTS

| 5,172,700 | A | * | 12/1992 | Bencini et al. ............... 600/564 |
| 5,242,458 | A | * | 9/1993 | Bendel et al. ................ 606/147 |
| 5,893,863 | A | * | 4/1999 | Yoon .............................. 606/170 |
| 5,964,780 | A | * | 10/1999 | Balazs ........................... 606/208 |
| 6,099,539 | A | * | 8/2000 | Howell et al. ................ 606/151 |
| 6,616,683 | B1 | * | 9/2003 | Toth et al. ...................... 606/207 |
| 6,623,482 | B2 | * | 9/2003 | Pendekanti et al. ........... 606/51 |
| 2006/0258954 | A1 | * | 11/2006 | Timberlake ............ A61B 10/06 600/564 |
| 2009/0005854 | A1 | * | 1/2009 | Huang et al. ................ 623/1.15 |
| 2009/0131976 | A1 |   | 5/2009 | Kowalski |
| 2010/0263500 | A1 | * | 10/2010 | Bannasch et al. .............. 81/487 |

FOREIGN PATENT DOCUMENTS

| DE | 102006009559 B3 | 5/2007 |   |
| EP | 1203640 A2 * | 5/2002 | ............... B25B 7/02 |

* cited by examiner

*Primary Examiner* — Diane Yabut
*Assistant Examiner* — Martin T. Ton
(74) *Attorney, Agent, or Firm* — Whitmyer IP Group LLC

(57) ABSTRACT

A medical instrument with a shaft, a handle positioned on the proximal end of the shaft, a tool positioned on the distal end of the shaft with two jaw members that can be displaced between an open and a closed position, and with an actuating element by which the handle and tool are in active connection with one another and where each jaw member of the tool consists of an inner cheek and an outer cheek, which are connected with one another on the distal end of each jaw member and are distanced from one another in the proximal direction, and at least one connecting brace is positioned between the inner cheek and the outer cheek. The medical instrument has jaw members, while preserving flexibility, have an increased dimensional stability, in particular with respect to torsion impact. The inner cheek and the outer cheek of each jaw member is configured differently with respect to the shape of their cross-section, with the inner cheek configured as wider than the outer cheek and with the inner cheek of each jaw member having rounded or stepped configuration.

16 Claims, 3 Drawing Sheets

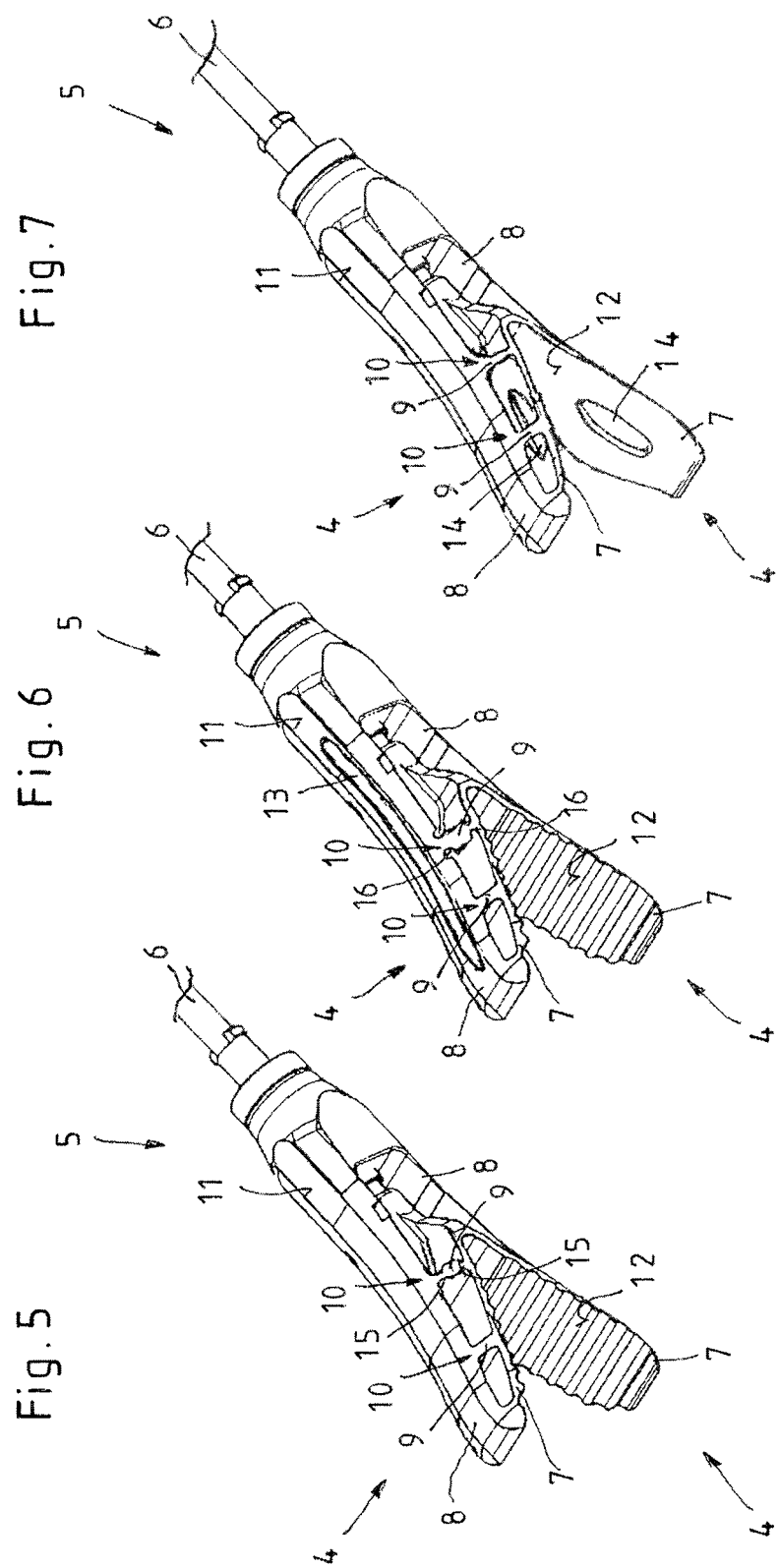

MEDICAL INSTRUMENT WITH SHAPE ADAPTIVE GRIPPING TOOL

CROSS-REFERENCE TO RELATED APPLICATIONS

The present application claims priority of German patent application No. 10 2010 009 259.2 filed on Feb. 25, 2010, the content of which is incorporated herein by reference.

FIELD OF THE INVENTION

The invention relates to a medical instrument, in particular for endoscopic purposes, with a shaft, a handle positioned on the proximal end of the shaft, a tool positioned on the distal end of the shaft, said tool having two jaw members that can be displaced between an open and a closed position, and with an actuating element by which the handle and the tool are in active connection with one another and so that every jaw member of the tool is configured as a jaw member that can be deformed by force impact and that consists of an inner cheek and an outer cheek, said cheeks being connected with one another on the distal end of each jaw member and distanced from one another in the proximal direction, so that between the inner and outer cheeks at least one linking brace is positioned.

BACKGROUND OF THE INVENTION

Medical instruments configured as gripping instruments are used in particular in endoscopic surgery to grasp tissue or comparable biological material. The gripping instruments customarily used in the art comprise rigid jaw members, which have no flexibility with respect to the object that is to be grasped. From the traction between the jaw members and the grasped object, point loads can develop that can cause damage to the grasped object, for example a blood vessel.

Patent DE 10 2007 026 721 A1 discloses a shape-adaptive medical gripping instrument, which makes use of the Fin Ray Effect to avoid these disadvantageous point loads between the jaw members of the gripping instrument and the grasped object and essentially to convert them into a form lock.

The Fin Ray Effect refers to a double-layered structure that performs a directed deformation through force impact, for example by sidestepping in the force contact point and at its ends turning against the force direction, and thus adapts to the shape of the object that induces the force.

Adaptive gripping tools known in the art have the disadvantage, however, that the inner and outer cheeks of the jaw members, produced from a flat binding material, have a low dimensional stability, in particular with respect to torsion impact.

On this basis, it is the object of the invention to provide a medical instrument of the aforementioned type, whose jaw members while maintaining flexibility have a high dimensional stability, in particular with respect to torsion impact.

SUMMARY OF THE INVENTION

This object is achieved according to a first embodiment of the invention whereby the inner cheek and outer cheek of each jaw member are configured differently with respect to the shape of their cross-section, so that the inner cheek is broader in configuration than the outer cheek and the outer cheek of each jaw member is configured as rounded or stepped on its outside.

The widening of the inner cheeks increases the gripping surface of this jaw member while simultaneously increasing the surface inertial moment of the inner cheeks. In addition, the rounded or stepped configuration of the outside of the outer cheeks causes an increase in dimensional stability. In particular with an endoscopic gripping instrument, this adaptation of the outer contour of the outer cheeks of the jaw members to the inner contour of the trocar sheath, by which the gripping instrument is guided into the surgical area, is advantageous because as a result the construction space is used to maximum possible advantage, which is also advantageous for the insulation of the trocar sheath.

According to a practical embodiment of the invention, it is proposed that the inner cheek and outer cheek of each jaw member should be configured differently, in addition, with respect to the choice of material.

The object of the invention is achieved, according to a second, alternative embodiment of the invention, in such a way that the inner cheek and outer cheek of each jaw member are configured differently with respect to the choice of material.

Because of the different configuration of the inner and outer cheeks of each jaw member with respect to the shape of the cross-section and/or the choice of material, it is possible to increase the surface inertial moment of individual cheeks and thus, while maintaining the shape-adaptive flexibility of the jaw members, to increase their dimensional stability, in particular their torsion stability.

It is further proposed with the invention that the at least one connecting brace between the inner and outer cheeks should be of trapezoidal configuration if the outer cheek is configured as narrower than the inner cheek. This trapezoidal configuration of the at least one connecting brace causes an additional torsion resistance of the jaw member that is so configured.

The dimensional stability of the cheeks can be further improved, according to the invention, if a reinforcement rib, running in the longitudinal direction of the jaw member, is configured on the outside of the outer cheek and/or on the gripping surface of the inner cheek of each jaw member In order to increase the flexibility of the jaw members despite the increased torsion rigidity of the inventively configured jaw members, it is further proposed with the invention that a window-type perforation should be configured in the outer cheek and/or in the inner cheek of each jaw member.

It is further proposed with the invention that, in addition or alternatively to the configuration of the different cross-section shapes of the two cheeks of each jaw member, the material of the inner cheeks should have greater rigidity than the material of the outer cheeks in order thereby to increase the torsion rigidity of the jaw members.

The different materials or properties of materials of the inner and outer cheeks can be obtained, for example, by two-component injection-molding, in which to achieve varying rigidities of the cheeks, fiber-reinforced materials, for example, are used for the more rigid cheek. Carbon nanotubes (CNTs), for instance, can be used as material for the fiber reinforcement.

The combination of different materials or material properties has the advantage that the configuration and operating action of the jaw members of the tool can be further varied. For example, the jaw members can be configured in such a way that the inner cheeks close nearly parallel to one another or else at first close, forceps-like, on the distal ends and form a hollow space in the middle of the gripping surfaces, depending on which gripping action of the tool is desired.

It is finally proposed with the invention that the inner cheeks of the two jaw members should be connected with one another at the proximal end. This connection point of the two inner cheeks of the jaw members forms an appropriate contact point for the actuating element, by which the jaw members can be displaced. Advantageously, the inner cheeks of the jaw members and the actuating element are configured as a one-piece injection-molded part, so that a direct connection, without play, exists between the actuating element and the tool that is to be displaced.

To simplify the manufacture of the jaw members or of the entire tool, it is further proposed with the invention that the inner cheek and the outer cheek of each jaw member or the inner cheeks and outer cheeks of both jaw members of the tool should be configured as a one-piece injection-molded part.

The deformability of the jaw members under force impact can be reinforced according to the invention by connecting the at least one connecting brace by solid-state joints with the inner cheek and the outer cheek, so that a relative movement of the two cheeks with respect to one another is facilitated.

According to a first inventive embodiment for configuring the solid-state joints, it is proposed that the solid-state joints should be configured as taperings in the connecting brace in the transition to the respective cheek.

According to a second practical embodiment of the invention it is proposed that the solid-state joints should be configured as rounded recesses in the connecting braces and/or in the respective cheek.

Finally, according to a third embodiment of the invention, it is proposed that the solid-state joints should be configured with varying material thickness in the transition from the connecting brace to the respective cheek.

It is further proposed with the invention that the inner cheeks and the outer cheeks of each jaw member should be connected with one another as a flat surface between their distally mutually connected ends and the distal-side first connecting brace.

Further properties and advantages of the invention can be seen from the appended drawings, in which four embodiments of an inventive medical instrument are presented in merely exemplary manner, without restricting the invention to said embodiments.

BRIEF DESCRIPTION OF THE DRAWINGS

FIG. 5 shows a perspective view of detail V, depicting a second embodiment.

FIG. 6 shows a view according to FIG. 5, but depicting a third embodiment.

FIG. 7 shows a view according to FIG. 5, but depicting a fourth embodiment.

DETAILED DESCRIPTION OF THE INVENTION

Figure 1:
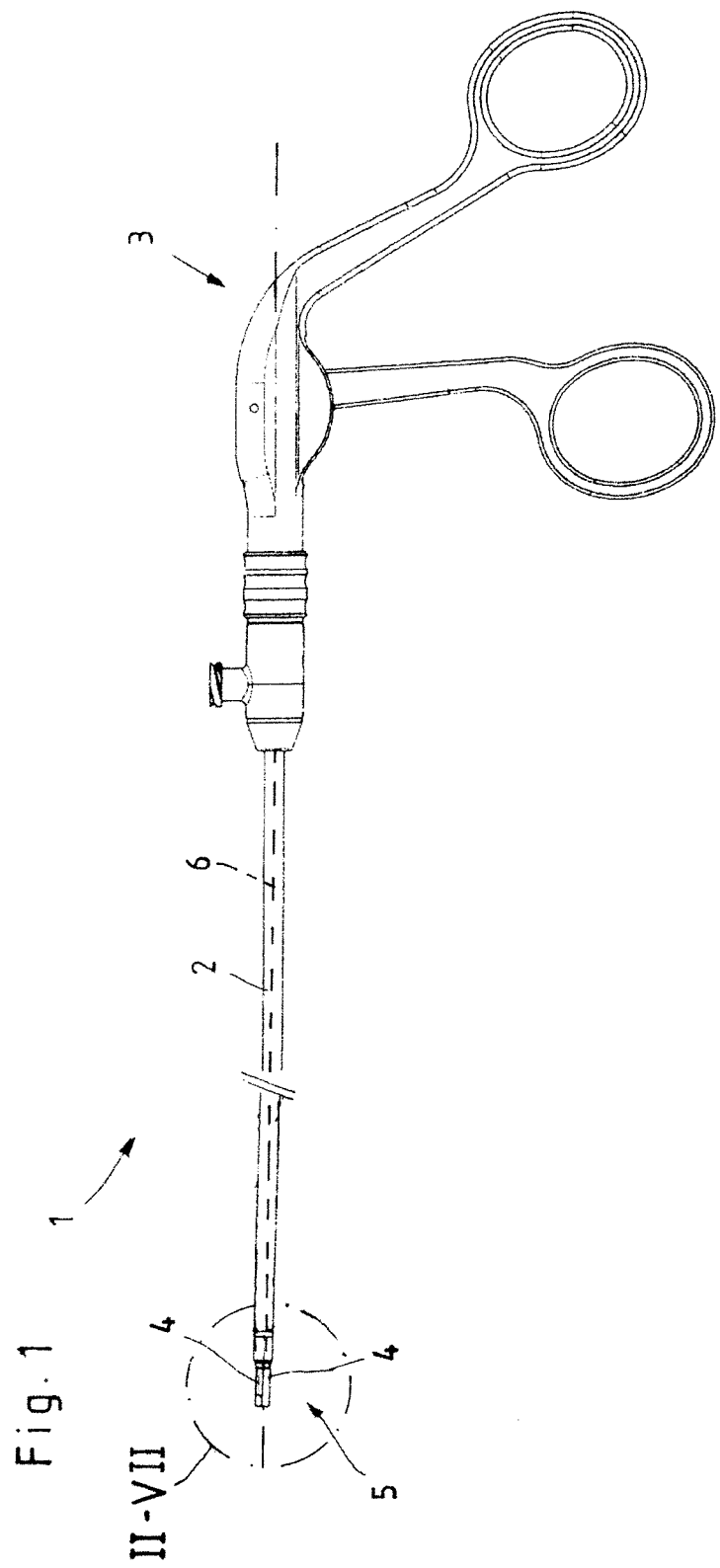
FIG. 1 shows a schematic side view of an inventive medical instrument.

The medical instrument 1 illustrated in FIG. 1 and configured as a gripping instrument consists essentially of a shaft 2 on whose proximal end a handle 3 is positioned and on whose distal end a tool 5 is configured consisting of two jaw members 4. To convert the jaw members 4 of the tool 5 from an open starting position into a closed position, the handle 3 and the jaw members 4 are in active connection with one another by way of an actuating element 6 mounted in the shaft 2.

As can be seen from FIG. 2 and FIGS. 5 through 7, every jaw member 4 of the tool 5 configured as a gripping tool 5 consists of an inner cheek 7 and an outer cheek 8, which are connected with one another on the distal end of each jaw member 4. The inner cheek 7 and the outer cheek 8 are configured at a distance from one another toward the proximal end of the jaw member 4, so that at least one connecting brace 9 is positioned between the inner cheek 7 and the outer cheek 8.

The inner cheeks 7 of the two jaw members 4 are connected with one another on their proximal ends as a contact point on the jaw member side for the actuating element 6 that serves to open and close the jaw members 4. The actuating element 6 configured as a push/pull element thus grips on the inner cheeks 7 of the two jaw members 4 and by exerting a tractive force on the inner cheeks 7 of the jaw member 4 causes the opening of the jaw members 4. Conversely, the exertion of a pulling force on the inner cheeks 7 of the jaw members 4 causes the jaw members 4 to open. In the illustrated embodiments the inner cheeks 7 are configured as cast directly onto the actuating element 6.

Alternatively to this embodiment of the inner cheeks 7 and of the actuating element 6 as a one-piece injection-molded part, it is also possible of course to connect the inner cheeks and the actuating element 6, for example, by cementing, riveting, bolting or other mechanical couplings.

The configuration of the jaw members 4 with the two cheeks 7 and 8, which are at a distance from one another and connected with one another only by at least one connecting brace 9, provides the necessary flexibility of the jaw members 4, which makes possible the opening and closing of the jaw member 4, as described above, by the application of a pulling or pushing force on the inner cheeks 7.

The flexibility of the jaw members 4 sufficient for configuring a shape-adaptive gripping tool can be obtained by having the inner cheeks 7 and outer cheeks 8 of the jaw members 4 connected with one another to configure the Fin Ray Effect by a framework of connecting braces 9. The Fin Ray Effect describes a two-layered structure (inner cheek 7 and outer cheek 8), which performs a directed deformation by force impact, sidesteps for example in the force impact point, and on its ends bends against the force direction and thus adapts to the shape of the object that is to induce the force.

Figure 3:
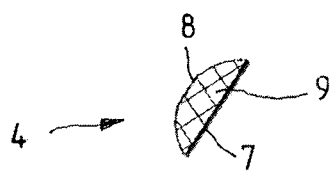
FIG. 3 shows a section along the line III-III in FIG. 2.

To be able to equip the jaw members 4 of the gripping tool 5 while maintaining their flexibility as required for the deformation with a sufficiently high dimensional stability, in particular with respect to torsion impacts, the inner cheek 7 and the outer cheek 8 of every jaw member 4 are of different configuration with respect to the cross-section shape and/or the material selection, as can be seen for example from the sectional view according to FIG. 3.

The deformability of the cheeks 7 and 8 of the jaw members 4 in the illustrated embodiments is further increased because the at least one connecting brace 9 is connected by solid-state joints 10 with the inner cheek 7 and the outer cheek 8, thus facilitating a relative movement of the two cheeks 7 and 8 with respect to one another.

Shown in FIG. 2 and FIGS. 5 through 7 are four embodiments for configuring the jaw members 4 of the gripping tool 5, which are distinguished from one another with respect to the means of generating the higher torsion rigidity of the jaw members 4 and/or of improving the flexibility of the jaw members 4.

In all the illustrated jaw members 4, the inner cheeks 7 are of wider configuration than the outer cheeks 8, so that by increasing the torsion rigidity the surface inertial moment of the inner cheek 7 is increased. In addition to the narrower configuration of the outer cheeks 8, the outer cheeks 8 of the jaw members 4 are configured as rounded on their outside 11.

Alternatively to the illustrated, essentially uniform rounding of the outside 11, it is also possible to configure the outside 11 in steps.

In particular, in using the medical gripping instrument 1 in endoscopic surgery, this adaptation of the outer contour of the outer cheeks 8 of the jaw members 4 to the inner contour of the trocar sheath, by which the gripping instrument 1 is guided into the surgical area, is advantageous because by this means the constructive space is used to best advantage, which is also advantageous for insulating the trocar sheath.

Figure 2:
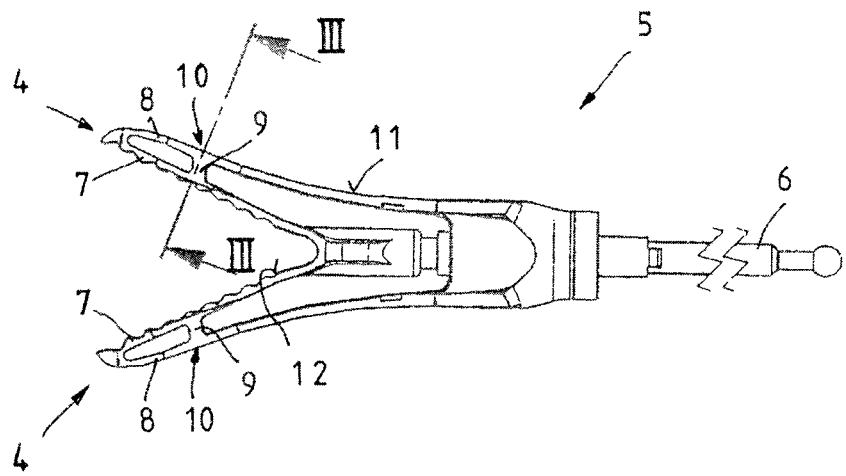
FIG. 2 shows an enlarged view of detail II from FIG. 1, depicting a first embodiment.
Figure 4:
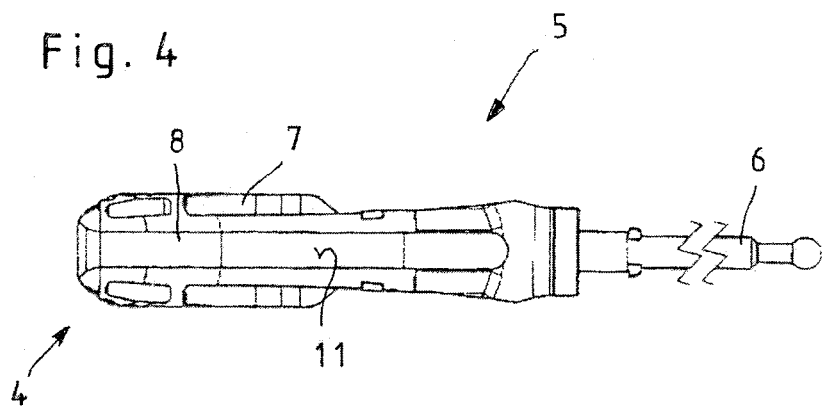
FIG. 4 shows an overhead view of the embodiment according to FIG. 2.

In FIGS. 2 through 4 a first embodiment is shown for configuring the jaw members 4 or inner cheeks 7 and outer cheeks 8 configured as described above. In this embodiment the inner cheek 7 and the outer cheek 8 are connected to one another by a connecting brace 9 or are kept at a distance from one another. As can be seen from the sectional view in FIG. 3, the connecting brace 9 is of trapezoidal configuration because of the different widths of the inner cheek 7 and outer cheek 8. This trapezoidal shape of the connecting brace 9 further increases the torsion resistance of the jaw member 4.

In the second embodiment, shown in FIG. 5, for configuring the jaw members 4 or the inner cheeks 7 and outer cheeks 8, two connecting braces 9 are positioned between the inner cheek 7 and the outer cheek 8. The illustrated number of connecting braces 9, namely only one connecting brace 9 according to FIG. 2 or two connecting braces 9 according to FIGS. 5 through 7, is given only as an example. It is also possible, of course, to use more than two connecting braces 9 and to position them differently as well, for example at an angle to one another. What is decisive is that the flexibility of the jaw members 4 should be maintained.

FIG. 5 shows, in addition, that the gripping surfaces 12 of the inner cheeks 7 in this embodiment are configured as grooved surfaces. Configuration of the gripping surfaces 12 in wavelike form is also possible and useful for corresponding applications. The grooved inner cheek 7 or the inner cheek 7 in wavelike form in connection with jaw members 4 of a synthetic material has the additional advantage that this configuration in turn changes the flexibility of the inner cheeks 7 and various possibilities result for determining the behavior of the jaw members 4.

In the third embodiment, shown in FIG. 6, for configuring the jaw members 4 or the inner cheeks 7 and outer cheeks 8, a reinforcement rib 13 running in the longitudinal direction of the jaw members 4 is positioned on the outsides 11 of the outer cheeks 8 in each case, said rib serving to further increase the torsion rigidity of the jaw members 4. Alternatively or in addition to the arrangement of one or more reinforcement ribs 13 on the outsides 11 of the outer cheeks 8, it is also possible of course to position one or more reinforcement ribs 13 running in the longitudinal direction of the jaw members 4 on the gripping surfaces 12 of the inner cheeks 7.

In the fourth embodiment, shown in FIG. 7, for configuring the jaw members 4 or the inner cheeks 7 and outer cheeks 8, a window-like perforation 14 is configured in the inner cheeks 7 to increase the flexibility of the jaw members 4. Alternatively or in addition to the configuration of one or more window-like perforations 14 in the inner cheeks 7 it is also possible of course to configure one or more window-like perforations 14 in the outer cheeks 8.

FIG. 7 also shows that the gripping surfaces 12 of the inner cheeks 7 in this embodiment are configured as level, smooth surfaces.

Alternatively and/or in addition to the change of the cross-section shape of the inner cheeks 7 and outer cheeks 8, it is also possible to achieve the torsion resistance through deliberate material selection for configuring the inner cheeks 7 and outer cheeks 8, for example by ensuring that the material of the inner cheeks 7 has a greater rigidity than the material of the outer cheeks 8.

The embodiments illustrated in FIGS. 5 through 7 are differentiated from one another further by the configuration of the solid-state joints 10 by which the connecting braces 9 are connected with the inner cheeks 7 and the outer cheeks 8.

In the second embodiment, shown in FIG. 5, the solid-state joints 10 of the connecting brace 9 positioned farther to the proximal side are configured as taperings 15 in the connecting brace 9 in the transition to the respective cheek 7 or 8.

On the other hand, in the third embodiment, shown in FIG. 6, the solid-state joints 10 are configured as rounded recesses 16 in the connecting brace 9 and in the respective cheek 7 or 8.

In the fourth embodiment, shown in FIG. 7, the solid-state joints 10 in the transition from the connecting brace 9 to the respective cheek 7 or 8 are configured with varying material thickness.

In addition to this constructive configuration of the solid-state joints 10, it is possible to configure the solid-state joints 10 in such a way that they alter their shape at excessive stress without, however, breaking, to prevent an excessive force transmission.

A medical gripping instrument 1 as described above is distinguished in that the jaw members 4 of the gripping tool 5, because of the particular configuration of the inner cheeks 7 and outer cheeks 8, have an increased dimensional stability with respect to the shape of the cross-section and/or the material selection of the jaw members 4, in particular with respect to the torsion resistance.

What is claimed is:

1. A medical instrument, in particular for endoscopic purposes, comprising:
    a shaft, a handle positioned on a proximal end of the shaft, a tool positioned on a distal end of the shaft with two jaw members that can be displaced between an open position and a closed position, and an actuating element by which the handle and the tool are in active connection with one another for opening and closing the jaw members,
    wherein every jaw member of the tool is configured as a jaw member that consists of an inner cheek and an outer cheek, which are connected with one another on a distal end of every jaw member and are at a distance from one another in a proximal direction,
    wherein the inner cheek and the outer cheek of every jaw member are connected with one another by a framework of at least one connecting brace which is positioned between the inner cheek and the outer cheek so that every jaw member can be deformed under force impact by deforming the inner cheek and the outer cheek of the respective jaw member, wherein the inner cheek and the outer cheek of each jaw member are configured differently with respect to a cross-section shape, so that the inner cheek is of wider configuration than the outer cheek and the outer cheek of each jaw member is rounded or stepped in configuration on its outside, wherein the at least one connecting brace is configured to have a first width dimension, the first width dimension being measured in a direction transverse to a longitudinal direction of each jaw member and along the inner cheek of each jaw member, the at least one connecting brace is configured to have a second width dimension being measured in the direction transverse to the longitudinal direction of each jaw member and along the outer cheek of each jaw member, said first width dimension being larger than the second width dimension, and wherein the inner cheeks of both jaw members are directly and transition-free connected with one another on their proximal ends as a contact point for the actuating element and wherein the inner cheeks are configured as cast directly onto the actuating element to achieve a direct connection free of play between the actuating element and the tool, and wherein the actuating element is configured as a push/pull element which is mounted in the shaft.

2. The medical instrument according to claim 1, wherein the inner cheek and outer cheek of every jaw member are of different configuration with respect to a material selection.

3. A medical instrument, in particular for endoscopic purposes, comprising:

a shaft, a handle positioned on a proximal end of the shaft, a tool positioned on a distal end of the shaft with two jaw members that can be displaced between an open position and a closed position, and an actuating element by which the handle and the tool are in active connection with one another for opening and closing the jaw members, wherein every jaw member of the tool is configured as a jaw member that can be deformed by force impact and that consists of an inner cheek and an outer cheek that are connected with one another on a distal end of each jaw member and are at a distance from one another in a proximal direction, wherein the inner cheek and the outer cheek of every jaw member are connected with one another by a framework of at least one connecting brace which is positioned between the inner cheek and the outer cheek, wherein the inner cheek and outer cheek of each jaw member are configured differently in configuration with respect to a choice of material, wherein the at least one connecting brace is configured to have a first width dimension, the first width dimension being measured in a direction transverse to a longitudinal direction of each jaw member and along the inner cheek of each jaw member, the at least one connecting brace is configured to have a second width dimension being measured in the direction transverse to the longitudinal direction of each jaw member and along the outer cheek of each jaw member, said first width dimension being larger than the second width dimension, wherein every jaw member can be deformed under force impact by deforming the inner cheek and the outer cheek of the respective jaw member, and wherein the inner cheeks of both jaw members are directly and transition-free connected with one another on their proximal ends as a contact point for the actuating element and wherein the inner cheeks are configured as cast directly onto the actuating element to achieve a direct connection free of play between the actuating element and the tool, and wherein the actuating element is configured as a push/pull element which is mounted in the shaft.

4. The medical instrument according to claim 1, wherein the at least one connecting brace is of trapezoidal configuration.

5. The medical instrument according to claim 1, wherein a reinforcement rib running in a longitudinal direction of the jaw member is configured on the outside of the outer cheek and/or of the gripping surface of the inner cheek of every jaw member.

6. The medical instrument according to claim 1, wherein a window-like perforation is configured in the outer cheek and/or in the inner cheek of every jaw member.

7. The medical instrument according to claim 1, wherein a material of the inner cheeks has a greater rigidity than a material of the outer cheeks.

8. The medical instrument according to claim 7, wherein the inner cheeks consist of a fiber-reinforced material.

9. The medical instrument according to claim 1, wherein the inner cheeks and the actuating element are configured as a one-piece injection-molded part.

10. The medical instrument according to claim 1, wherein the inner cheek and the outer cheek of at least one of the jaw members is configured as a one-piece injection-molded part.

11. The medical instrument according to claim 10, wherein the inner cheeks and the outer cheeks of both jaw members of the tool are configured as a one-piece injection-molded part.

12. The medical instrument according to claim 1, wherein the at least one connecting brace is connected with the inner cheek and outer cheek by solid-state joints.

13. The medical instrument according to claim 12,
wherein the at least one connecting brace has a thickness dimension measured in the longitudinal direction of each jaw member, and
the thickness dimension tapers at the solid state joints from a middle of the at least one connecting brace towards the inner cheek and from the middle of the at least one connecting brace towards the outer cheek.

14. The medical instrument according to claim 12, wherein the solid-state joints are rounded recesses in the at least one connecting brace, the rounded recesses include rounded recesses adjacent to the outer cheek and rounded recesses adjacent to the inner cheek.

15. The medical instrument according to claim 12, wherein the solid-state joints are configured in the transition from the connecting brace to the respective cheek with varying thickness of material.

16. A medical instrument, in particular for endoscopic purposes, comprising:
a shaft,
a handle positioned on a proximal end of the shaft,
a tool positioned on a distal end of the shaft, the tool having two jaw members that are displaceable between an open position and a closed position, and
an actuating element connecting the handle with the tool to open and close the jaw members, the actuating element being a push/pull element mounted in the shaft,
each jaw member of the tool having an inner cheek and an outer cheek, the inner cheek and the outer cheek being connected with one another at a distal end of the respective jaw member and diverging from one another in a proximal direction, wherein, for each jaw member, the inner cheek and the outer cheek are connected with one another by a framework of at least one connecting brace positioned between the inner cheek and the outer cheek so that the jaw member is deformable under force impact by deforming the inner cheek and the outer cheek, wherein, for each jaw member, the inner cheek and the outer cheek are configured differently with respect to cross-sectional shape, so that the inner cheek is wider than the outer cheek, wherein the inner cheeks of the jaw members are directly and transition-free connected with one another at proximal ends thereof as a contact point for the actuating element, the inner cheeks being cast directly onto the actuating element, wherein a perforation is formed in at least one of the jaw members, the perforation extending from an inner surface of the outer cheek to an outer surface of the outer cheek, and/or from an inner surface of the inner cheek to an outer surface of the inner cheek.

* * * * *